United States Patent [19]

Sugihara et al.

[11] 4,342,779
[45] * Aug. 3, 1982

[54] 7-ACETYLSPIROBENZOFURANONE COMPOUND

[75] Inventors: Hirosada Sugihara, Osaka; Masazumi Watanabe; Mitsuru Kawada, both of Hyogo; Isuke Imada, Osaka, all of Japan

[73] Assignee: Takeda Chemical Industries, Ltd., Osaka, Japan

[ * ] Notice: The portion of the term of this patent subsequent to Aug. 18, 1998, has been disclaimed.

[21] Appl. No.: 257,316

[22] Filed: Apr. 17, 1981

Related U.S. Application Data

[63] Continuation-in-part of Ser. No. 115,548, Jan. 25, 1980, Pat. No. 4,284,644, which is a continuation-in-part of Ser. No. 968,520, Dec. 11, 1978, abandoned.

[30] Foreign Application Priority Data

Dec. 27, 1977 [JP] Japan ............................ 52-159177
Jun. 19, 1978 [JP] Japan ............................ 53-74700
Nov. 6, 1978 [JP] Japan ............................ 53-136967
May 4, 1979 [JP] Japan ............................ 54-55082
Jun. 25, 1979 [JP] Japan ............................ 54-80551
Apr. 23, 1980 [GR] Greece ............................ 61757
Mar. 30, 1981 [JP] Japan ............................ 56-48286

[51] Int. Cl.$^3$ .................... A61K 31/34; C07D 307/94
[52] U.S. Cl. .................................... 424/285; 549/330
[58] Field of Search .................... 260/346.22; 424/285

[56] References Cited

U.S. PATENT DOCUMENTS

4,105,670 8/1978 Noguchi et al. ............ 260/326.11 R

OTHER PUBLICATIONS

Okitsu et al., Heterocycles, vol. 6, No. 11, (1977).
Donnelly et al., Chem. and Ind. (1967) pp. 1402–1403.

*Primary Examiner*—Henry R. Jiles
*Assistant Examiner*—Bernard Dentz
*Attorney, Agent, or Firm*—Wegner & Bretschneider

[57] ABSTRACT

Novel 7-acetylspirobenzofuranone compound of the formula:

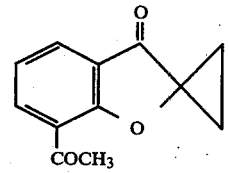

has gastric secretion inhibitive, antiinflammatory and analgesic activities, and is of value as drugs.

3 Claims, No Drawings

7-ACETYLSPIROBENZOFURANONE COMPOUND

This application is a continuation-in-part of application Ser. No. 115,548, filed Jan. 25, 1980 now U.S. Pat. No. 4,284,644, which is a continuation-in-part of application Ser. No. 968,520, filed Dec. 11, 1978, now abandoned.

This invention relates to 7-acetylspirobenzofuranone compound and use of said compound.

The present compound is 7-acetylspiro[benzo[b]furan-2(3H), 1'-cyclopropane]-3-one having the formula (I):

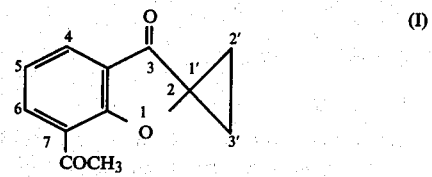

The compound (I) of the present invention can be produced, for example, by subjecting a compound of the formula (II):

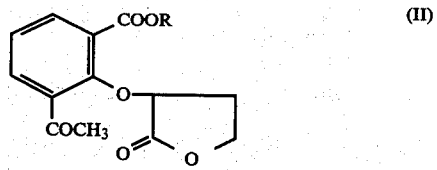

wherein R is $C_{1-4}$alkyl, to condensation and decarboxylation in one pot with an organic base and a catalyst which assists decarboxylation.

Referring to the formula (II), examples of the $C_{1-4}$alkyl group R include methyl or ethyl.

In the above reaction, the organic base is employed to promote ester-condensation i.e. Dieckmann condensation and the decarboxylating catalyst is employed to promote decarboxylation of the condensed compound [the formula (III) described hereinafter]. Preferred examples of said organic base include tertiary amines (e.g. triethylamine, 1,4-diazabicyclo[2,2,2]octane or 1,8-diazabicyclo[5,4,0]-7-undecene). Preferred examples of said catalyst which assists decarboxylation include metal halides (e.g. sodium chloride, sodium bromide, sodium iodide, potassium bromide, potassium chloride, potassium iodide, etc.) and quaternary ammonium salts (e.g. tetramethylammonium bromide, etc.). The reaction temperature is normally about 100° C. to 200° C. and preferably about 140° C. to 160° C., although the reaction may be conducted at higher or lower temperatures if it is desired to control the reaction velocity. Purging the reaction vessel with an inert gas (e.g. $N_2$, argon) is sometimes effective in preventing side reactions and improving yields. This reaction is normally carried out in a suitable solvent. While any solvent that will not interfere with the reaction may be employed, it is normally advantageous to employ a solvent having a boiling point higher than the reaction temperature (e.g. dimethyl sulfoxide, N,N-dimethylformamide, hexamethylphosphoramide).

The compound (I) of the present invention can be produced also by subjecting a compound of the formula (III):

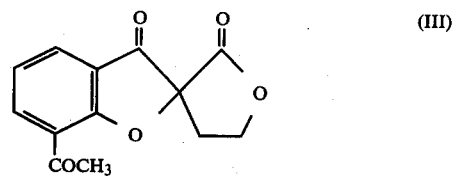

to decarboxylation.

This reaction is carried out in the presence of the above-mentioned decarboxylating catalyst and under similar reaction conditions to those described in the condensation and decarboxylation reaction of the compound (II) but absence of the organic base which promotes ester condensation.

The contemplated compound (I) obtained in the foregoing manner can be isolated from the reaction mixture and purified by conventional procedures (e.g. distillation, recrystallization or column chromatography).

The spiro compound (I) according to this invention is a new compound which exhibits gastric secretion inhibitive, antiinflammatory, analgesic and other effects in mammals (e.g. man, rat, mouse, guinea-pig, dog and pig), for instance, a intraduodenal administration of 50 mg/kg of the compound (I) in rats shows strong suppression of gastric secretion and of ulcer formation induced by water-immersion restraint stress, and the compound (I) is less toxic. Therefore, it is of value as antiulcer, antiinflammatory, analgesic and as drugs for the management of peptic ulcer, acute or chronic gastritis, lumbago, arthritis and other diseases. Management of a peptic ulcer in accordance with the present invention includes both the prophylactic administration of the spiro compound (I) to prevent the outbreak of an ulcer in an ulcer prone patient, as well as the treatment of an existing peptic ulcer. In such medicinal applications, the compound (I) can be safely administered orally or parenterally, either as it is or as formulated with pharmaceutically acceptable carriers or diluents known per se into suitable dosage forms such as tablets, powders, capsules, injections and suppositories. While the recommended dosage depends on the subject, condition, route of administration, etc., the normal oral dosage for the treatment of peptic ulcer or acute or chronic gastritis is about 1 mg. to 20 mg. as compound (I) per kg body weight per dose, to be given once to 3 times daily.

The starting compounds (II) and (III) which are employed in the practice of this invention can be prepared by the following route of synthesis or any process analogous thereto.

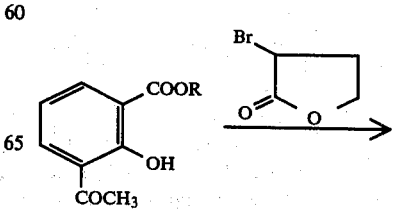

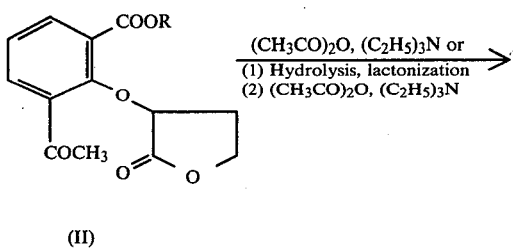

(II)

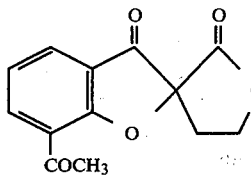

(III)

wherein R is as defined hereinbefore.

The carboxy-substituted spiro compound in Reference Example 2 described hereinafter can be produced by subjecting the present compound (I) to oxidation and said compound including its pharmaceutically acceptable salts (e.g. sodium or potassium salt) has the same utility as that of the present compound (I).

The following reference and working examples are intended to describe this invention in further detail but should not be considered as limiting the scope of this invention in any way.

REFERENCE EXAMPLE 1

To a mixture of methyl 3-acetylsalicylate (5.8 g) and potassium carbonate (10.4 g) in acetone (200 ml) was added α-bromo-γ-butyrolactone (12.5 g) under stirring, and the mixture was refluxed for 11 hours. The insolubles were filtered off and the filtrate was concentrated under reduced pressure. The residue was subjected to chromatography on silica gel eluting with chloroform. By the above procedure, there was obtained α-[(6-acetyl-2-methoxycarbonylphenyl)oxy]-γ-butyrolactone as pale yellow oil.

Infra red absorption spectrum (IR) $\nu_{max}^{film}$ cm$^{-1}$: 1780 (γ-lactone), 1720 (COOCH$_3$), 1690 (COCH$_3$)

Elemental analysis, for $C_{14}H_{14}O_6$: Calcd.: C, 60.43; H, 5.07: Found: C, 60.21; H, 5.02.

EXAMPLE 1

A mixture of α-[(6-acetyl-2-methoxycarbonylphenyl)oxy]-γ-butyrolactone (3.5 g), 1,8-diazabicyclo[5,4,0]-7-undecene (0.14 g) and sodium chloride (1.1 g) in N,N-dimethylformamide (66.5 ml) was stirred at 150°–160° C. for 5 hours. The solvent was distilled off under reduced pressure and the residue was subjected to chromatography on silica gel. The fraction eluted with dichloromethane was recrystallized from CHCl$_3$-hexane to give 7-acetylapiro[benzo[b]furan-2(3H), 1'-cyclopropane]-3-one (0.22 g) as colorless needles melting at 114°–115° C.

Elemental analysis, for $C_{12}H_{10}O_3$: Calcd.: C, 71.28; H, 4.99: Found: C, 71.39; H, 4.96.

Reference Example 2

A mixture of 7-acetylspiro[benzo[b]furan-2(3H), 1'-cyclopropane]-3-one (86 mg), 2.4 ml of aqueous solution of sodium hypochlorite and a small amount of surface active agent (polyoxyethylene octyl phenyl ether) was stirred at 60° C. for 2 hours. After cooling, the reaction mixture was diluted with water, and to the mixture was added 40% aqueous solution of sodium hydrogen sulfite. The reaction mixture was made acidic with hydrochloric acid, and resulting crystals were extracted with ethyl acetate. After washing with water and drying, the solvent was distilled off under reduced pressure. The residue was recrystallized from ethanol to give colorless needles of 7-carboxyspiro[benzo[b]furan-2(3H), 1'-cyclopropane]-3-one. m.p. 259°–262° C. (decomp). Sublime at 183° C.

$IR\nu_{max}^{KBr}$ cm$^{-1}$: 1730 (COOH), 1680 (CO). NMR(CD$_3$OD)δ: 1.67 (2H, t, J=3 Hz, CH$_2$), 1.93 (2H, t, J=3 Hz, CH$_2$), 7.37 (1H, t, J=8 Hz, 5-aromat.H), 8.02 (1H, dd, J=2 Hz, 8 Hz, 4- or 6-aromat.H), 8.40 (1H, dd, J=2 Hz, 8 Hz, 4- or 6-aromat.H).

Elemental analysis, for $C_{11}H_8O_4$: Calcd.: C, 64.70; H, 3.95: Found: C, 64.53; H, 4.00.

Examples of preparations ready for administration

When the compound of this invention is intended for use as an anti-ulcer drug, types of suitable preparations can be exemplified as follows.

| 1. Tablet | |
|---|---|
| (1) 7-Acetylspiro[benzo[b]furan-2(3H, 1'-cyclopropane]-3-one | 50 g. |
| (2) Lactose | 50 g. |
| (3) Corn-starch | 29 g. |
| (4) Magnesium stearate | 1 g. |
| 1000 tablets | 130 g. |

Components (1) and (2) and 17 g. of the corn-starch (3) were granulated together with a paste prepared from 7 g. of the corn-starch. To these granules were added the remaining 5 g. of the corn-starch and component (4). The mixture was then compressed by a tabletting machine to prepare 1000 tablets of 7 mm. diameter, each containing 50 mg. of (1).

| 2. Capsule | |
|---|---|
| (1) 7-Acetylspiro[benzo[b]furan-2(3H), 1'-cyclopropane]-3-one | 50 g. |
| (2) Lactose | 100 g. |
| (3) Cellulose fine powder | 45 g. |
| (4) Magnesium stearate | 5 g. |
| 1000 capsules | 200 g. |

All the materials were mixed and filled into 1000 capsules (gelatin capsule No. 3 defined in Japanese Pharmacopoeia, 8th edition) to prepare capsules each containing 50 mg. of (1).

What is claimed is:

1. 7-Acetylspiro[benzo[b]furan-2(3H), 1'-cyclopropane]-3-one.

2. A pharmaceutical composition for managing peptic ulcer which comprises, as an active ingredient, an effective amount of 7-acetylspiro[benzo[b]furan-2(3H), 1'-cyclopropane]-3-one and a pharmaceutically acceptable carrier or diluent therefor.

3. A method of managing peptic ulcer in a patient which comprises administering to said patient 7-acetylspiro[benzo[b]furan-2(3H), 1'-cyclopropane]-3-one, said compound being administered in an amount effective to manage peptic ulcer in said patient.

* * * * *